United States Patent [19]

Bele

[11] Patent Number: 4,641,660

[45] Date of Patent: Feb. 10, 1987

[54] ECHOGRAPHY PROBE AND APPARATUS INCORPORATING SUCH A PROBE

[75] Inventor: Robert Bele, Chessy, France

[73] Assignee: CGR Ultrasonic, Meaux, France

[21] Appl. No.: 660,997

[22] Filed: Oct. 15, 1984

[30] Foreign Application Priority Data

Oct. 18, 1983 [FR] France ................................ 83 16550

[51] Int. Cl.[4] ................................................ A61B 10/00

[52] U.S. Cl. ........................................ 128/660; 73/626

[58] Field of Search ................ 367/153; 128/660, 661; 73/625–626

[56] References Cited

U.S. PATENT DOCUMENTS 4,203,162 5/1980 Clearwaters et al. .

4,307,613 12/1981 Fox ................................ 128/660 X 4,328,569 5/1982 Trott et al. ...................... 367/153 X 4,409,982 10/1983 Plesset et al. ........................ 128/660

FOREIGN PATENT DOCUMENTS 2052918 1/1981 United Kingdom .

*Primary Examiner*—Kyle L. Howell
*Assistant Examiner*—Francis J. Jaworski
*Attorney, Agent, or Firm*—Pollock, VandeSande & Priddy

[57] ABSTRACT

An echography apparatus comprising a probe reconstituting mobile rings by element switching, said probe comprising a plurality of transducer elements spread over a convex coupling surface, and switching means being provided for grouping together certain transducer elements into rings.

13 Claims, 9 Drawing Figures

FIG_2-a
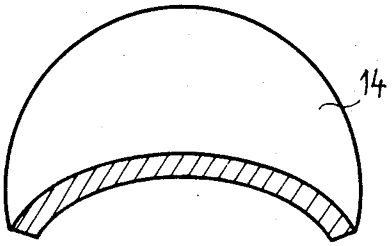
FIG_2-b
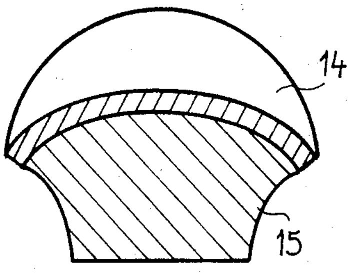
FIG_2-c
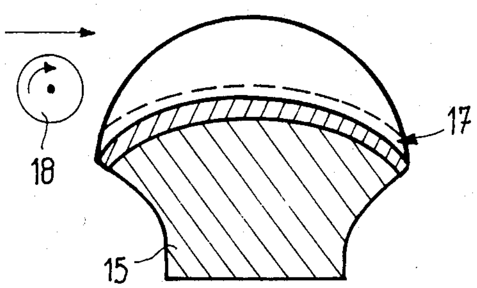
FIG_2-d
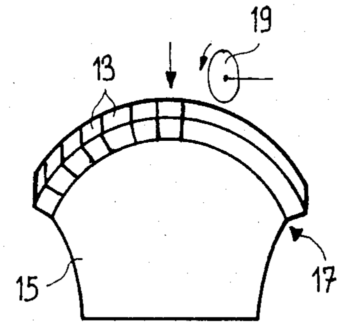
FIG_2-e
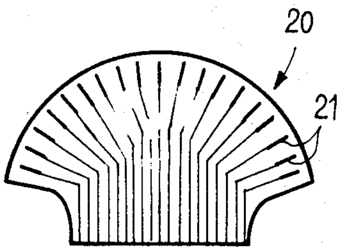

ECHOGRAPHY PROBE AND APPARATUS INCORPORATING SUCH A PROBE

BACKGROUND OF THE INVENTION

1. Field of the Invention

The invention relates to a new type of static echographY probe and the process for manufacturing such a probe. The invention also relates to an echography apparatus incorporating such a probe.

2. Description of the Prior Art

The most widely used echography probes at the present time are sectorial sweep probes, that is to say comprising either an oscillating mobile assembly or several transducers mounted on a wheel and switched as they travel past an emission window. The qualities of these probes are their speed of acquisition and their fundamental simplicity which results in relatively simple and inexpensive signal processing means. The coupling surface is relatively small, so that the probe may be disposed between two ribs of the patient for cardiac observation. On the other hand, the life span of these probes is limited.

Systems using liner arrays of transducer elements are essentially reserved for observing adominal regions, because of the large dimensions of the probe. In these systems, the elements (or groups of elements) are successively switched so as to provide a sweep perpendicular to the row of elements. The technology of linear array probes has been used for observations of the thoracic cage, by reducing the coupling surface of the probe and distributing delays (on emission as at reception) between the transducer elements of the array so as to reconstitute a sectorial sweep, i.e. so as to emit and receive in convergent directions inscribed in a sweep range. This technology, known under the name of phased array, provides a static probe whose coupling surface has sides of no more than 20 mm. However, the processing electronic equipment is very expensive. In fact, the delays to be provided (by delay lines, on the reception side at least) may reach 10 microseconds and an acceptable control of the directivity is only possible if these delays are provided with a tolerance of 10 nanoseconds. Now, at the present time, such an accuracy is obtained only for delays of two to three microseconds at most. To overcome this problem, a frequency change may be operated, then the signals received converted into digital information; and predetermined delay laws may be applied to the digital information. The electronic circuits for operating the frequency change represent a considerable part of the price of the equipment.

Furthermore, a type of ring transducer probe is known in which the beam is generated by a group of transducer elements in the form of concentric rings. This arrangement has the advantage of a Bessel function "antenna diagram" (18 dB attenuation of the secondary lobes with respect to the main lobe). Proposals have even been made for reconstituting such rings from a flat transducer element array, so as to cause movements of these rings providing an ultrasonic mission sweep in a predetermined direction. This has the drawback of creating expensive and cumbersome probes, (like the linear arrays). Furthermore, the coupling is mediocre.

SUMMARY OF THE INVENTION

The purpose of the invention is first of all to provide a static probe structure ensuring under all circumstances excellent coupling of the transducer elements with the body of the patient, with a reduced coupling surface for, more especially, examining the inside of the thoracic cage (by passing between the ribs) and with which a sectorial sweep may be effected, at least partially by movement of the rings.

To this end, the invention provides then an echography probe comprising a mosaic of transducer elements covering at least a part of the convex coupling surface.

With respect to the above described system known under the name of phased array, the probe of the invention has more especially the advantage of generating the sectorial sweep essentially by switching transducer elements and not exclusively by delay laws. The coupling is moreover much better and the secondary lobes are attenuated by 18 dB if a ring configuration is adopted. As will be seen further on, the invention also provides for several emission-reception sequences for each position of the rings, by defining a limited number of microangulations, using appropriate delay laws between the elements of the rings. However, in this case, the delays brought into play are much smaller and so technologically easier to achieve with delay lines, with the required accuracy.

The invention also provides a process for manufacturing an echography probe characterized in that it consists:

in molding an insulating support on the internal surface of a piezoelectric material having a convex external surface, in cutting slices of substantially constant width from the assembly formed by said block of piezoelectric material and the insulating support, in partially cutting said slices at regular intervals along the directions perpendicular to their convex curved surfaces, by severing the whole of said piezoelectric material each time so as to define a curved row of individualized transducer elements in each slice, in fixing on each side of each slice a printed circuit comprising as many individualized conductors as there are transducer elements in said slice so that each conductor is in contact with a transducer element side, and in assembling and fixing said slices side by side in order so as to reconstitute a mosaic of transducer elements spaced apart over a convex surface.

The invention also relates to a variant of this process in which curved slices of piezoelectric material are individualized before molding an insulating support on the concave internal surface of each slice.

The invention finally relates also to an echography apparatus of the type comprising a fixed transducer probe, said probe comprising a mosaic of transducer elements defining a convex coupling surface and further comprising switching means for grouping transducer elements selectively together in a configuration defining approximately concentric rings and for causing said configuration to move in an alternating sweep and first means for associating a first delay law with different rings.

This first delay law, applied to the rings, defines the focal characteristics an emission-reception sequence (dynamico focusing occuring both at an emission step and at a reception step. For increasing the number of lines of the reconstituted image, the echography apparatus advantageously comprises second means for associating additional delay laws with the different transducer elements of each ring. These additional delay laws which relate to the elements of the same ring bring into play shorter delays than the first law, and it is these laws which determine the microangulations on each side of the normal to the coupling surface passing through the center of the ring configuration. In other words, if the first law alone is applied to the rings, the firing takes place along this normal and the additional delay laws determine for each firing a given microangulation with respect to this normal. Each possible position of the ring configuration may then give rise to several firings and so to several lines of the reconstituted image.

BRIEF DESCRIPTION OF THE DRAWINGS

The invention will be better understood and other advantages thereof will be clearer from the following description of a probe, a process for manufacturing this probe and an echography apparatus incorporating the probe, given solely by way of example and with reference to the accompanying drawings in which.

FIGS. *2a, 2b, 2c, 2d* and *2e* illustrate steps in the process for manufacturing such a probe.

DESCRIPTION OF THE PREFERRED EMBODIMENT

Figure 1:
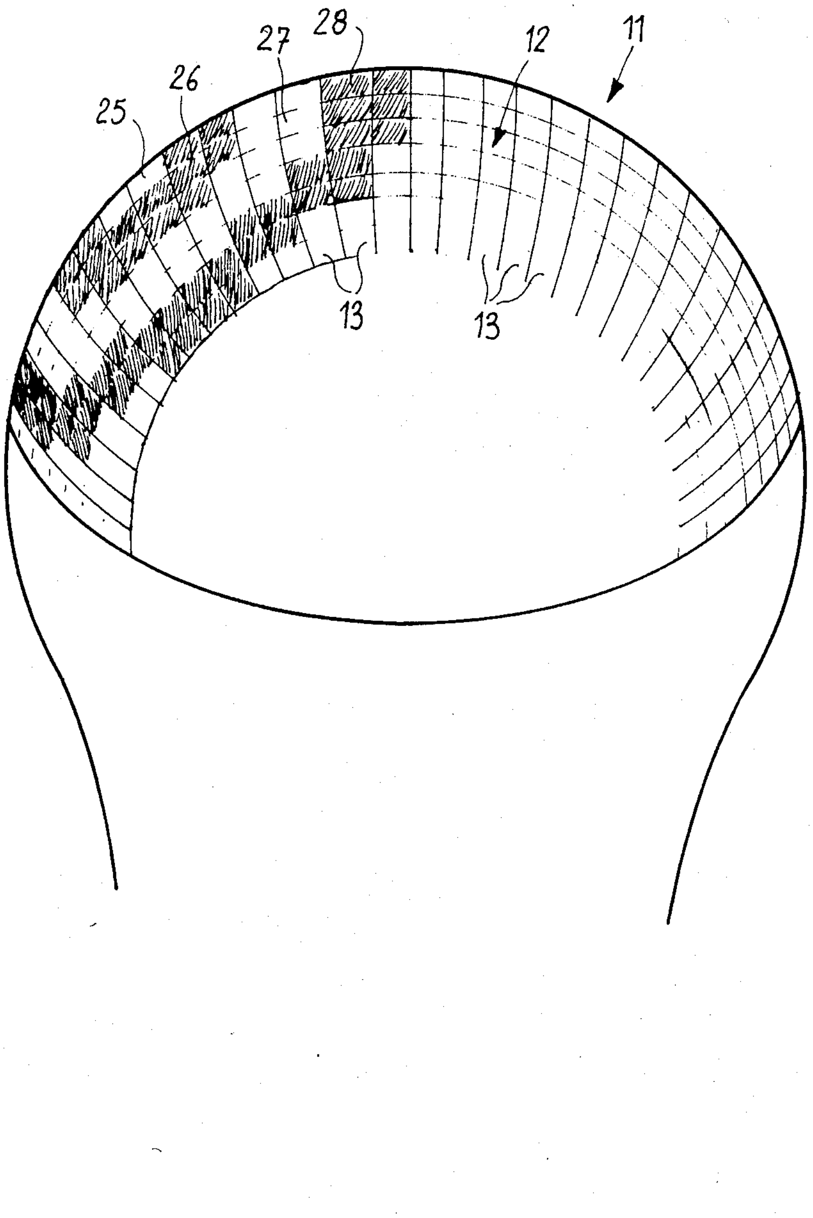
FIG. 1 shows a probe in accordance with the invention.
Figure 4:
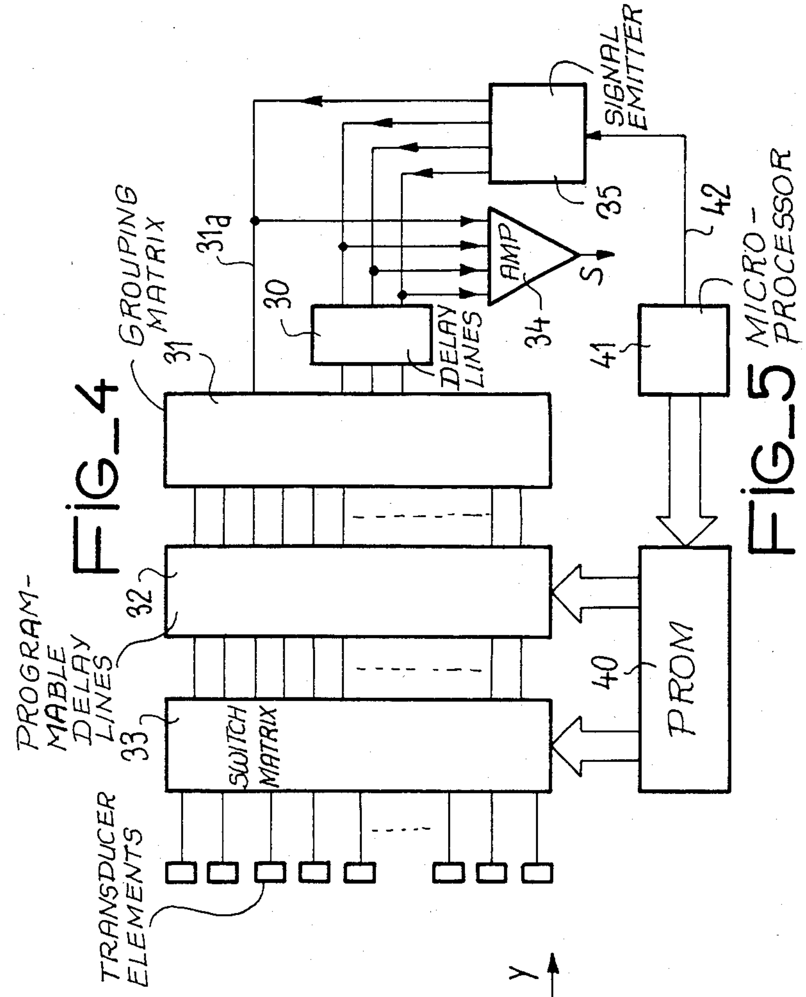
FIG. 4 is a block diagram of an echography apparatus operating with the probe of FIG. 1.

In FIG. 1 has been shown the end part of an echography probe 11 in accordance with the invention, whose coupling surface 12 (i.e. the surface intended to be placed in contact with the subject to be examined) is convex and formed partially of a mosaic of transducer elements 13. In this example, the general shape of the coupling surface is that of a spherical skull cap because it is one of the shapes which is most suitable for providing good coupling between the probe and the patient. However, other similar shapes could be suitable, as for example paraboloids or ellipsoids of revolution. A cylindrical convex surface may also be envisaged since one of the preferred methods of use of the probe (which will be described further on) consists in selecting and switching the transducer elements so as to cause an approximately concentric ring configuration to move from one side to the other of the probe. A cylindrical surface having a mosaic strip of a width equal to the diameter of the largest ring could therefore be suitable.

For the same reason, the spherical skull cap, paraboloid or ellipsoid embodiments are not necessarily provided with a mosaic over the whole of their coupling surface, a mosaic strip is sufficient for the type of use with ring sweep operation.

Structurally, the probe may be formed of the side by side assembly of slices each comprising a curved row of transducer elements, said slices having different mean radii of curvature.

FIG. 2 illustrates one way of constructing such a probe. It may be advantageous to start with a block of piezoelectric material in the shape of a spherical skull cap 14 (FIG. *2a*) since such shapes are currently used in ultrasonic techniques for different systems. An insulating support 15 is molded against the concave face of the spherical skull cap 14 (FIG. *2b*); the techniques for molding these supports are well known to a man skilled in the art. Slices 17 are then cut parallel to each other from a median strip of the spherical skull cap (FIG. *2c*) using for example a very fine saw 18. These slices therefore have different mean radii of curvature. Once the slices have been individualized, they are partially severed at regular intervals (*2d*) along directions perpendicular to their convex curved surface. Saw 19 is therefore adjusted so as to sever each time the whole of the piezoelectric material (by slightly nicking the insulating support) so as to define a curved row of individualized transducer elements 13. in each slice. Concurrently, printed circuits 20 are manufactured (FIG. *2e*) comprising as many individualized conductors 21 as the slices comprise transducer elements. Then two printed circuits of this kind are fixed (for example by bonding) on each side of each slice, so that each conductor 21 is in contact with a side of a transducer element 13. Then said slices are reassembled in the same order as for cutting up (i.e. so as to reconstitute a mosaic of transducer elements distributed over a relatively regular convex surface) and they are fixed side by side, for example by bonding.

At this stage in the manufacture of the probe, we have therefore as many pairs of electric conductors as there are individualized transducer elements. In the case when a ring sweep is desired, it should be noted that the delay laws applicable are the same for the transducer elements symmetric with respect to a plane of symmetry of the coupling surface perpendicular thereto and in which the desired path of the center of the ring configuration is inscribed. Consequently, the conductors connected to the transducer elements symmetrical with respect to this plane may advantageously be connected in parallel or in series (preferably directly inside the head of the probe) which reduces by half the number of wires to be connected to the electronic unit processing the signals.

Figure 3:
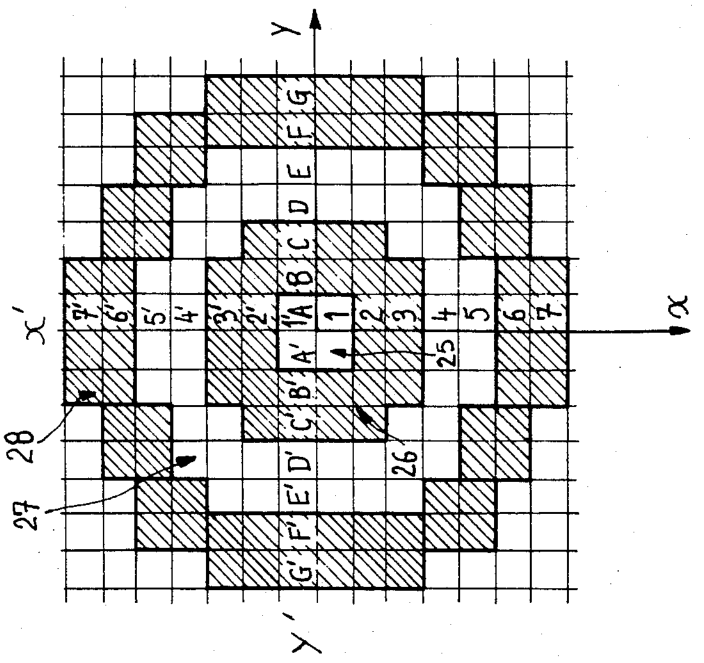
FIG. 3 is a top view of the ring configuration caused to move on the surface of the probe of FIG. 1.

FIG. 3 shows a possible configuration with three concentric rings 26, 27 and 28 (plus the central part 25); this configuration is also illustrated in FIG. 1 in a possible sweeping position. The central part 25 comprises four elements, the first ring 26 comprises 28, the second ring 27 comprises 52 and the third ring 28 comprises 72.

For each emission-reception or firing sequence, the electronic processing system must then first of all select 156 transducer elements adjacent to each other, for each position of the rings. The ring configuration occupies 14 transducer elements in the vicinity of the above mentioned plane of symmetry, in the direction of movement of the rings. Moreover, if the diameter of the coupling surface is 30 mm (supposing that it is a half sphere) and if the pitch for cutting up the transducer elements is 1.5 mm, the two slices the nearest to the plane of symmetry will have 30 or so elements. The number of possible positions of the ring configuration will therefore be 16.

By programming a first delay law between the different rings (the central part 25 being assimilated to one of them), very directive focusing may be obtained with a beam emitted perpendicularly to the coupling surface from the center of the configuration. Calculation of these delays is within the scope of a man skilled in the art. They correspond to the compensation of the different propagation times of the ultrasounds emitted from different rings situated in different planes (since it may be considered that each ring is inscribed in the same plane for a spherical coupling surface) so that the wave front following the normal to the center of the ring configuration benefits from a good phase concordance, in the firing direction between the contributions of the different rings. These delays are of the order of from 1 to 3 microseconds. They are thus technologically feasible with a good accuracy of the order of ten nanoseconds. These are the longest delays which must be used. The cost price of corresponding delay lines is however not prohibitive and in any case these lines are only in a limited number (three in the example described). The delays are applied from the outer ring. In other words, the energization of the outer ring (at emission) forms the reference from which the different delays are counted before energization of the following rings.

Considering more particularly the ring configuration of FIG. 3, the first above mentioned delay law may be "improved" by selecting each ring in two stages, since they have a "width" corresponding to two transducer elements. Thus different delays may be applied to the internal and external elements of each ring, which is tantamount to considering that the configuration of FIG. 3 comprises in fact six rings, although the shapes of these rings are then much more approximative, more especially close to the center. It is also possible to vary the number of rings depending on the desired penetration depth and also to change the number of rings in the same firing sequence, between emission and reception.

However, we saw above that the number of possible positions of the ring configuration is only 16 in the example described. This is why, in each position of the rings, a certain number of microangulations may be formed on each side of the normal. Thus, four right hand microangulations and four left hand microangulations give eight additional lines for each position of the ring configuration, i.e. an image formed of 144 lines. Referring again to FIG. 3, in which the ring configuration is centered on an orthonormed reference x o y, where the axis x' o x1 designates the sweep direction and where the different elements are shown by FIGS. 1, 2, 3, etc. . . . positively and by FIGS. 1', 2', 3', etc. . . . negatively along this axis and by letters A, B, C, etc. . . . positively and A', B', C', etc. . . . negatively along the axis y' o y, the order of energization of the different elements may be the following for a "left hand" microangulation considering the drawing:

RING 28:

B7 and B'7-A7 and A'7-D6 and D'6-C6 and C'6-B6 and B'6-A6 and A'6-F5 and F'5-E5 and E'5-D5 and D'5-C5 and C'5-F4 and F'4-E4 and E'4-G3 and G'3-F3 and F'3-G2 and G'2-F2 and F'2-G1 and G'1-F1 and F'1-G1' and G'1'-F1' and F'1'-G2' and G'2'-F2' and F'2'-G3' and G'3'-F3' and F'3'-F4' and F'4'-E4' and E'4'-F5' and F'5'-E5' and E'5'-D5' and D'5'-C5' and C'5'-D6' and D'6'-C6' and C'6'-B6' and B'6'-A6' and A'6'-B7' and B'7'-A7' and A'7'-

RING 27:

B5 and B'5-A5 and A'5-D4 and D'4-C4 and C'4-B4 and B'4-A4 and A'4-E3 and E'3-D3 and D'3-C3 and C'3-E2 and E'2-D2 and D'2-E1 and E'1-D1 and D'1'-E1' and E'1'-D1' and D'1'-E2' and E'2'-D2' and D'2'-E3' and E'3'-D3' and D'3'-C3' and C'3'-D4' and D'4'-C4' and C'4'-B4' and B'4'-A4' and A'4'-B5' and B'5'-A5' and A'5'-

RING 26

B3 and B'3-A3 and A'3-C2 and C'2-B2 and B'2-A2 and A'2-C1 and C'1-B1 and B'1-C1' and C'1'-B2' and B'2'-A2' and A'2'-B3' and B'3'-A3' and A'3'.

CENTRAL PART 25:

A1 and A'1 - A1' and A'1'.

For a "right hand" microangulation the elements need to be energized in the reverse order. The simultaneously selected elements are those which are interconnected in the probe head, as mentioned above.

So 35 delays are counted for the outer ring 28, 25 delays for ring 27, 11 delays for ring 26 and one for the central part 25, i.e. a total of 72 delays.

The values of these delays depend on the desired microangulation. Use may therefore be made of a set of programmable delay lines and a switching matrix for associating the elements concerned (for a ring configuration) with the delays which are assigned thereto. This arrangement will be described further on. The calculation of the delays is within the scope of a man skilled in the art. They correspond simply to the compensation of the different propagation times of the ultrasounds emitted from different elements so that the wave front in the direction of the desired microangulation benefits from a good phase concordance between the contributions of the transducer elements.

One possible example of an echography apparatus capable of operating with the above described probe will now be described. This apparatus comprises a first group 30 of delay lines (These lines provide a few relatively long delays, intended to be applied between the rings), a grouping matrix 31 for associating the delays of group 30 with the different rings, a second group 32 of programmable delay lines (72 in number according to the example if FIG. 3) and a switching matrix 33 interconnected between the delay lines of group 32 and the different transducer elements (grouped together symmetrically in pairs) of the mosaic. The system further comprises a summing amplifier 34 grouping together the reception signals at the outputs of the delay line group 30 as well as at an independent access of matrix 31 (connection 31*a*) corresponding to the outer ring to which no delay is applied at this level. An ultrasonic signal emitter 35 is also connected to the delay lines of group 30 and to connection 31*a*. The system described uses then the delay lines and the matrices 31 and 33 not only for emitting but also for reception but a variant could be envisaged in which these matrices and delay lines would be used only for reception and where the emission delays would be provided by a control logic coupled to a plurality of emitters, each emitter being directly connected to a pair of symmetrical transducer elements.

The switching matrix 33 may be formed from an assembly of analog multiplexers connected in cascade, such that any pair of the transducer elements of the mosaic may be connected to any delay line of group 32. If we refer again to the preceding example, matrix 33 will comprise 210 accesses on the probe side and 72 accesses on the delay line group 32 side. Groups of analog multiplexers of the DG507 type, commercialized by SILICONIX, could for example be used connected in cascade. Each of these units comprises 16 analog switches connected together so as to have 16 inputs and a common output. Switching of the switches is controlled by an integrated decoder, with five inputs, receiving coded digital information. For each access of delay line group 32, a first stage of such units may be provided in number sufficient for connection to all the pairs of transducer elements, assembled in groups of 16, and a second stage (a single unit) combining at its inputs the outputs of the first stage, the output of the second stage being connected to one of the delay lines of group 32.

Figure 5:
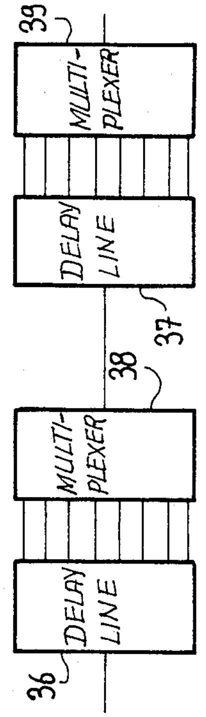
FIG. 5 shows a basic delay line structure.

These latter are programmable, that is to say that the value of the delays may be modified. A basic structure of such a delay line is shown in FIG. 5. It is subdivided into two lines 36, 37 with multiple outputs (for example eight), each output corresponding to a predetermined delay. Line 36 supplies a range of "short" delays whereas line 37 supplies a range of "long" delays. Two analog multiplexers 38 and 39 with eight inputs and one output have their inputs connected respectively to the outputs of lines 36 and 37. The output of multiplexer 38 is connected to the input of line 37.

The structure of the grouping matrix 31 is very simple.

Its role is in fact only to "recognize" the elements belonging to the different rings. It is therefore only a static grouping matrix, which determines four groups among the accesses to the delay lines of group 32 and connects three of them to the three delay lines of group 30, respectively and the fourth to the summing amplifier 34 and to the ultrasonic emitter 35. The delay lines of group 30 do not need to be programmable.

The delay lines are programmed at each emission-reception sequence by adding a delay value to a line 36 and a delay value to a line 37, and so on for each of the 72 programmable delay lines of group 32. These delay values depend on the desired microangulation. The role of matrix 33 is to select all the elements corresponding to a given position of the ring configuration on the mosaic and to "associate" them with the different delays.

For that, the apparatus is completed by a programmable memory 40 (PROM) into which the program for addressing matrix 33 and the delay line group 32 is written once and for all. Sequencing of the reading of this memory is controlled by a microprocessor 41 which also controls switching on of the emitter 35 (pilot connection 42). Amplifier 34 adds together the signals representative of the echos received and to which the same delay laws as at emission have been applied (focusing at reception). The output signals of amplifier 34 (output S) are processed, more especially "windowed" before being used as video signals in a television receiver on which the image is reconstituted line by line.

Memory 40 contains all the orders for successive addressing of matrix 33 and the delay line group 32 for complete scanning of the ring configuration on the surface of the probe. In other words, an emission-reception sequence is generated after positioning of the analog multiplexers of the matrix 33 selecting the position of the ring configuration on the mosaic and after programming the different delay lines of group 32, depending on the desired microangulation value. Matrix 33 remains in this state for nine firings (four microangulations to the right, four microangulations to the left and one normal to the surface). The delays are modified, still by partial reading of memory 40 after each firing. Then memory 40 drives the switching matrix 33 so as to cause the ring configuration to progress in the direction of the sweep, by a distance corresponding to the width of a transducer element and the microangulation sequence begins again. These operations are renewed until a complete image of 144 lines has been acquired in a complete sweep.

What is claimed is

1. An ultrasonic echography apparatus comprising:

a fixed transducer probe, the probe including:

transducer means for defining a convex coupling surface, said transducer means including a mosaic of transducer elements, switching means for selectively grouping a first set of transducer elements in said mosaic of transducer elements to form a configuration approximately defining concentric rings, the switching means further selectively grouping different sets of transducer elements in the mosaic, thereby effecting the moving of the configuration in an alternating sweep manner; and first means for applying a first delay law to each ring of the concentric rings for compensating the different propagation times for energies emitted from each ring of the concentric rings.

2. An ultrasonic echography apparatus according to claim 1 further comprising:

second means for applying additional delay laws to different transducer elements of each ring of the said concentric rings.

3. An ultrasonic echography apparatus according to claims 1 or 2, wherein the said convex coupling surface is in the form of a spherical skull cap.

4. An ultrasonic echography apparatus according to claim 1, said transducer element mosaic further comprising:

slices of piezoelectric material assembled side-by-side, each of the said slices including a curved row of transducer elements; and wherein the said slices have different mean radii of curvatures.

5. An ultrasonic echography apparatus according to claim 4, further comprising:

two conductors respectively fixed laterally to two sides of each said transducer element said transducer element mosaic having a plane of symmetry, the said conductors of the transducers symmetrical with respect to said plane of symmetry of the said transducer element mosaic being interconnected for connecting the respective transducer elements in parallel.

6. An ultrasonic echography apparatus according to claim 4, further comprising:

two conductors respectively fixed laterally to two sides of each said transducer element said transducer element mosaic having a plane of symmetry, the said conductors of the transducers symmetrical with respect to said plane of symmetry of the said transducer element mosaic being interconnected for connecting the respective transducer elements in series.

7. An ultrasonic echography apparatus according to claim 4, further comprising:

two printed circuits having individualized conductors, the conductors of one of said printed circuits being fixed on each side of each of said slices so that, for each said transducer element of each said curved row, two conductors belonging to different printed circuits are in contact with the sides of the said transducer element.

8. An ultrasonic echography apparatus according to claim 5 or 6, further comprising:

two printed circuits having individualized conductors, the conductors of one of said printed circuits being fixed on each side of each of said slices so that, for each transducer element of each said curved row, said two conductors belonging to different printed circuits are in contact with the said two conductors fixed to the sides of the transducer element.

9. An ultrasonic echography apparatus comprising:

means for forming a convex coupling surface, including slices of piezoelectric material assembled side-by-side into a mosaic of transducer elements, each of said slices including a curved row of transducer elements, said slices having different mean radii of curvatures;

switching means for selectively grouping a first set of transducer elements in said mosaic of transducer elements to form a configuration approximately defining concentric rings, said the switching means further selectively grouping different sets of transducer elements in the mosaic, thereby effecting the moving of the configuration in an alternating sweep manner; and means for applying a first delay law to each ring of the concentric rings for compensating the different propagation times for energies emitted from each ring of the concentric rings.

10. An ultrasonic echography apparatus according to claim 9, further comprising:

two conductors respectively fixed laterally to two sides of each said transducer element said transducer element mosaic having a plane of symmetry, the said conductors of the respective transducer elements transducers symmetrical with respect to said plane of symmetry of the said transducer element mosaic being interconnected for connecting the transducers in parallel.

11. An ultrasonic echography apparatus according to claim 9, further comprising:

two conductors respectively fixed laterally to two sides of each said transducer element said transducer element mosaic having a plane of symmetry, the said conductors of the transducers symmetrical with respect to said plane of symmetry of the said transducer element mosaic being interconnected for connecting the transducers in series.

12. An ultrasonic echography apparatus according to claim 9, further comprising:

two printed circuits having individualized conductors, the conductors of one of said printed circuits being fixed on each side of each of said slices so that, for each transducer element of each said curved row, two conductors belonging to different printed circuits are in contact with the sides of the transducer element.

13. An ultrasonic echography apparatus according to claims 10 or 11, further comprising:

two printed circuits having individualized conductors, the conductors of one of said printed circuits being fixed on each side of each of said slices so that, for each transducer element of each said curved row, two conductors belonging to different printed circuits are in contact with the two conductors fixed to the sides of the transducer element.

* * * * *